United States Patent [19]
Fuller et al.

[11] Patent Number: 5,968,033
[45] Date of Patent: Oct. 19, 1999

[54] OPTICAL DELIVERY SYSTEM AND METHOD FOR SUBSURFACE TISSUE IRRADIATION

[75] Inventors: Terry A. Fuller, Rydal; Aarne H. Reid, Meadowbrook, both of Pa.

[73] Assignee: Fuller Research Corporation, Rydal, Pa.

[21] Appl. No.: 08/962,858

[22] Filed: Nov. 3, 1997

[51] Int. Cl.⁶ .............................. A61N 5/06; A61B 17/36
[52] U.S. Cl. .................... 606/9; 606/16; 606/17
[58] Field of Search ................... 606/9, 13, 15, 606/16, 17; 607/88, 89

[56] References Cited

U.S. PATENT DOCUMENTS

| | | | |
|---|---|---|---|
| 4,461,947 | 7/1984 | Ward | 219/121 FS |
| 4,519,390 | 5/1985 | Horne . | |
| 4,539,987 | 9/1985 | Nath et al. . | |
| 4,592,353 | 6/1986 | Daikuzono . | |
| 4,676,231 | 6/1987 | Hisazumi et al. | 128/6 |
| 4,693,244 | 9/1987 | Daikuzono . | |
| 4,736,743 | 4/1988 | Daikuzono . | |
| 5,057,104 | 10/1991 | Chess | 606/9 |
| 5,282,797 | 2/1994 | Chess | 606/9 |
| 5,308,318 | 5/1994 | Plassche, Jr. | 604/54 |
| 5,344,418 | 9/1994 | Ghaffari | 606/9 |
| 5,348,552 | 9/1994 | Nakajima et al. | 606/16 |
| 5,359,685 | 10/1994 | Waynant et al. | 385/35 |
| 5,361,316 | 11/1994 | Tanaka et al. | 385/35 |
| 5,403,308 | 4/1995 | Wood et al. | 606/16 |
| 5,415,655 | 5/1995 | Fuller et al. | 606/16 |
| 5,474,549 | 12/1995 | Ortiz et al. | 606/9 |
| 5,514,125 | 5/1996 | Lasser et al. | 606/16 |
| 5,520,681 | 5/1996 | Fuller et al. | 606/17 |
| 5,595,568 | 1/1997 | Anderson et al. | 606/9 |
| 5,611,795 | 3/1997 | Slatkine et al. | 606/3 |
| 5,782,825 | 7/1998 | Anderson | 606/16 |
| 5,784,508 | 7/1998 | Turner | 606/16 |
| 5,843,152 | 12/1998 | Tu et al. | 606/41 |

*Primary Examiner*—Linda C. M. Dvorak
*Assistant Examiner*—Sonya Harris
*Attorney, Agent, or Firm*—Seidel Gonda Lavorgna & Monaco, PC

[57] ABSTRACT

An apparatus and method for optically treating tissue by contact between the apparatus and the tissue. The apparatus includes a holder having a distal end having an opening in it, and a contact member for contacting tissue to be treated and for coupling optical energy from a source of optical energy into said tissue. The contact member is a curved lens mounted in and partially extending from the opening and freely rotatable about at least one axis relative to the holder. The holder has a single coolant flow channel proximal to the opening and the contact member for supplying a cooling fluid to the contact member. A gap is provided between the contact member and the opening for allowing the fluid to flow around substantially the entire outer surface of the contact member and out of the opening onto said tissue to cool the tissue. The method includes the steps of contacting the surface of tissue in an area to be treated with a light transmissive low-friction contact optical element, applying optical energy from a source thereof to said optical element, converging said optical energy by said optical element into subsurface tissue in said area, moving said optical element over said area while maintaining it in contact with said surface, flowing a cooling fluid over said optical element and said surface to cool said optical element and said surface, and terminating application of optical energy to said optical element after a selected treatment time.

23 Claims, 8 Drawing Sheets

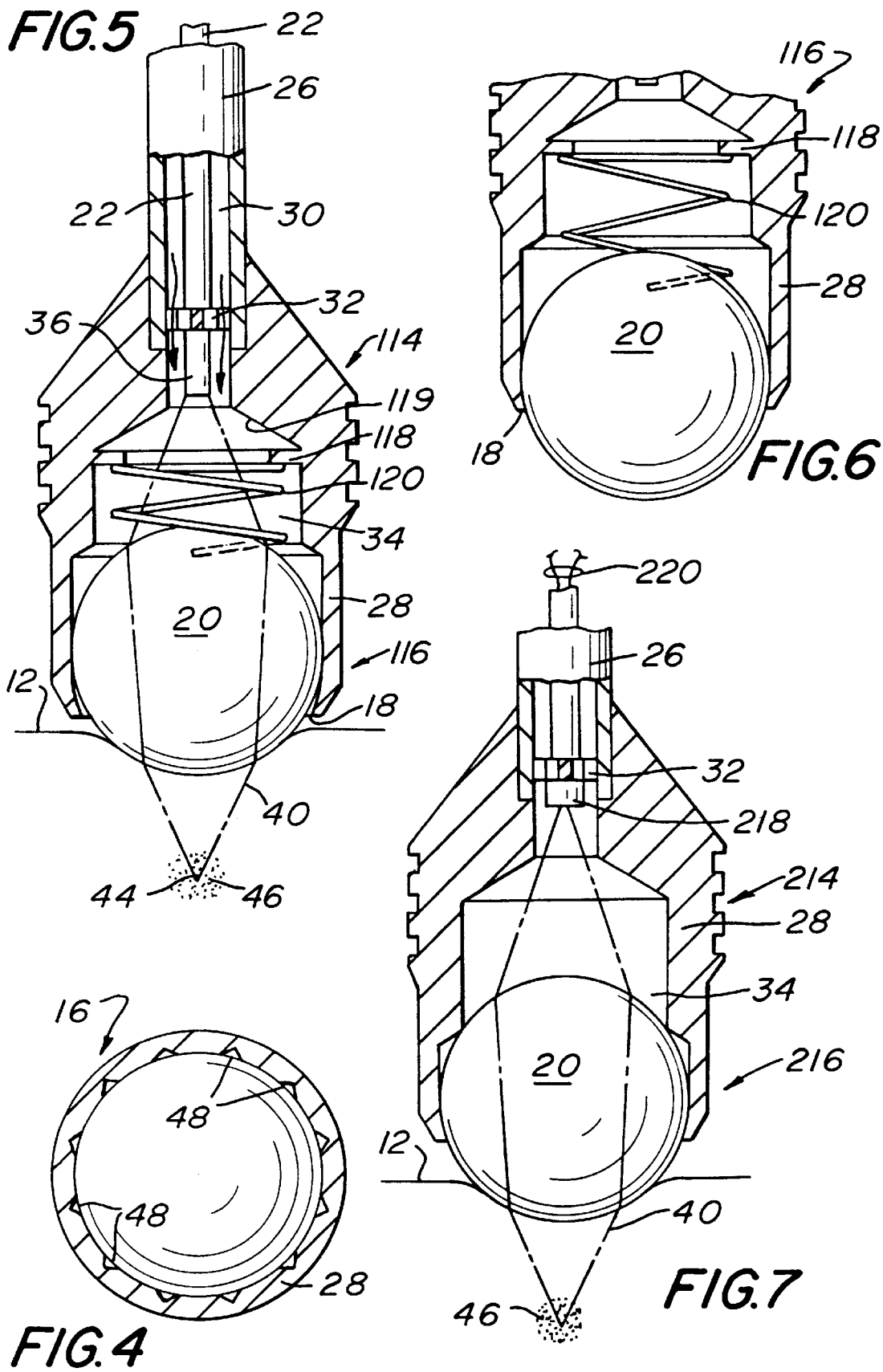

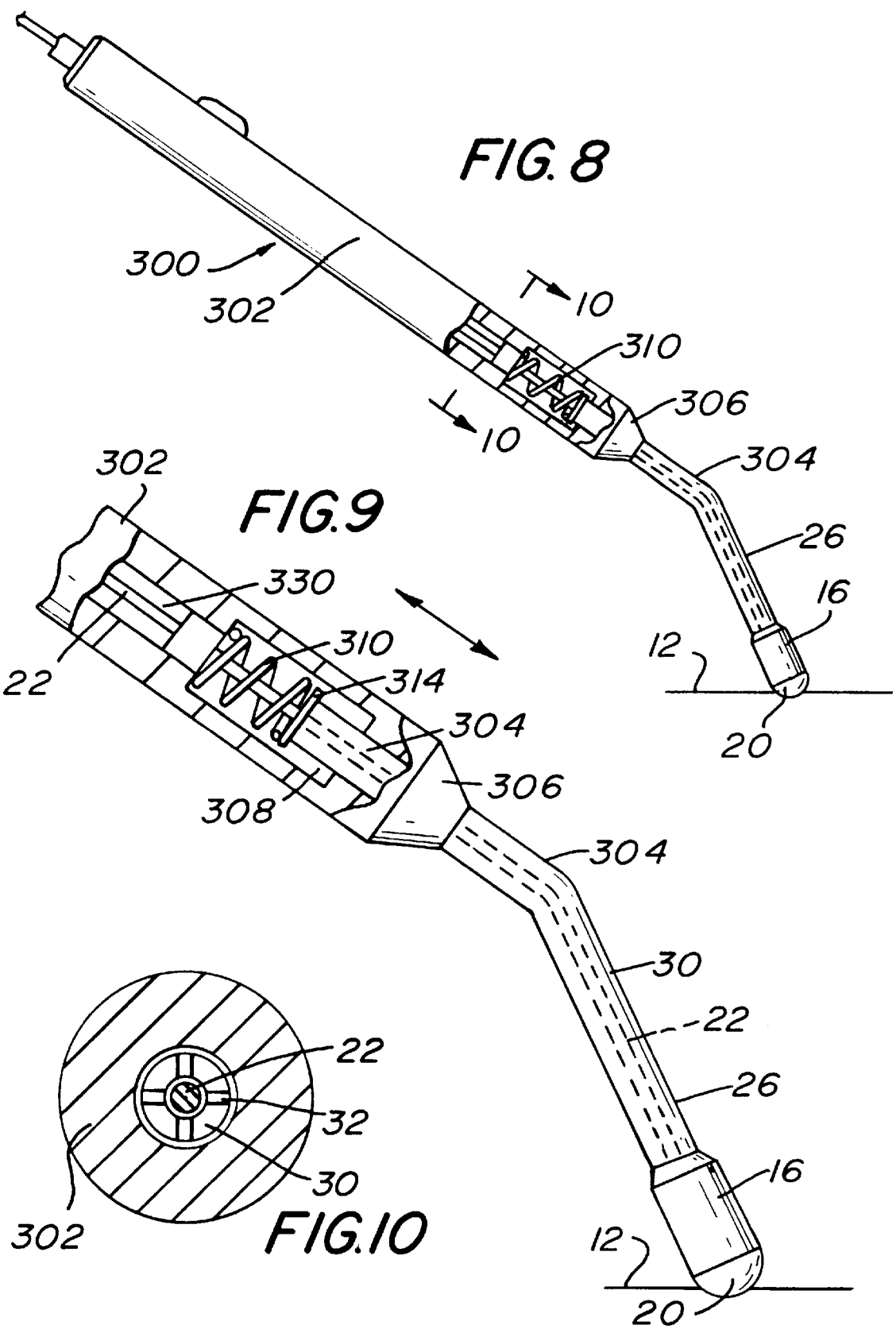

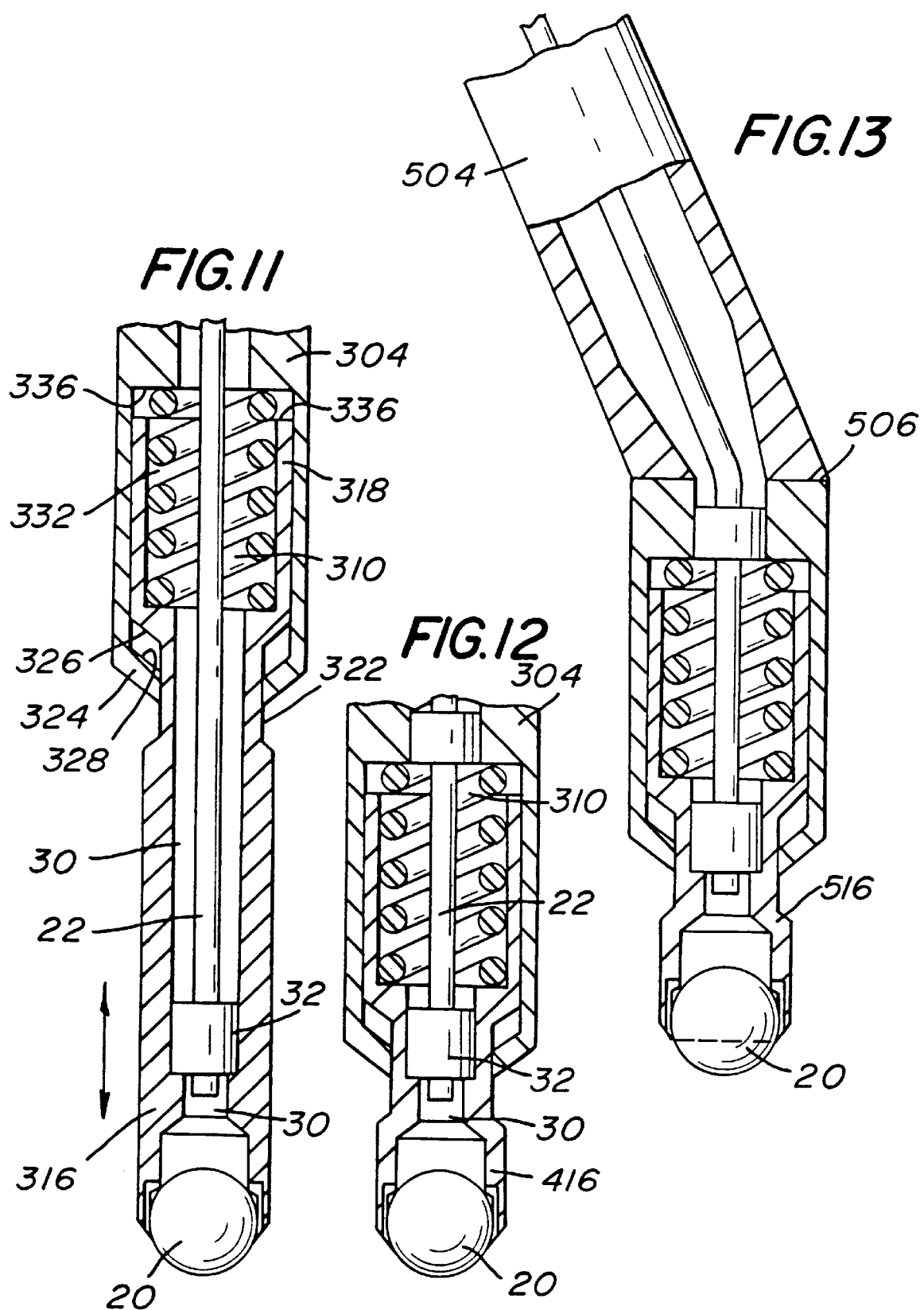

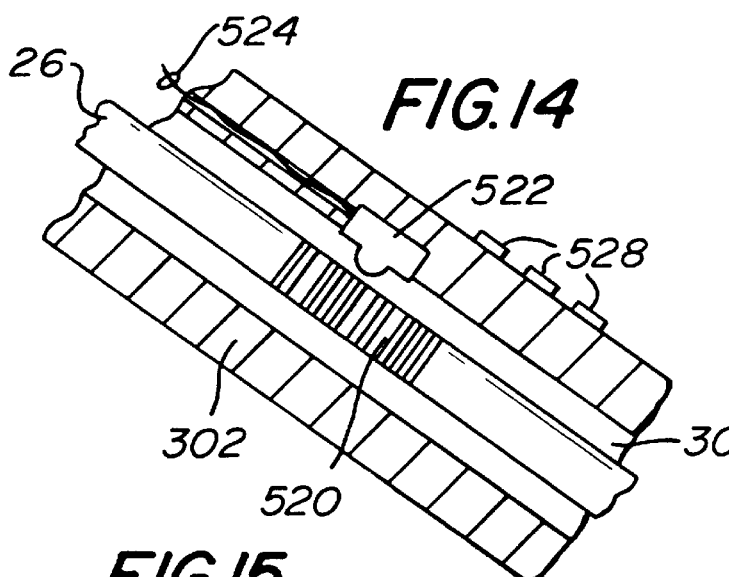
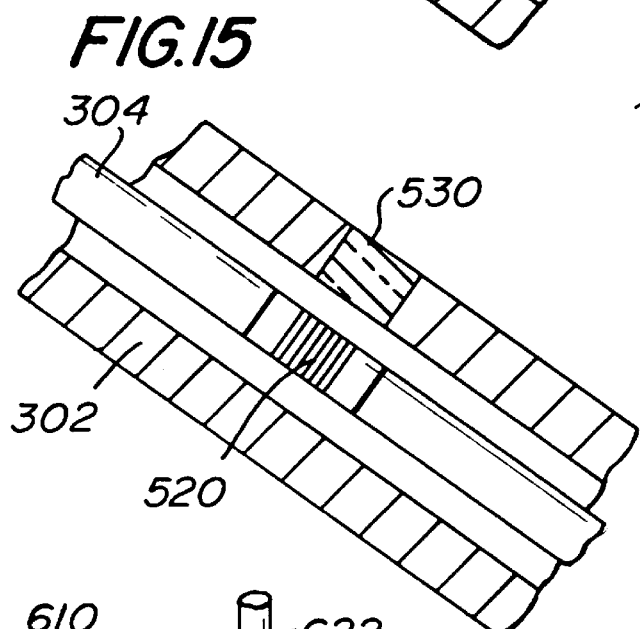
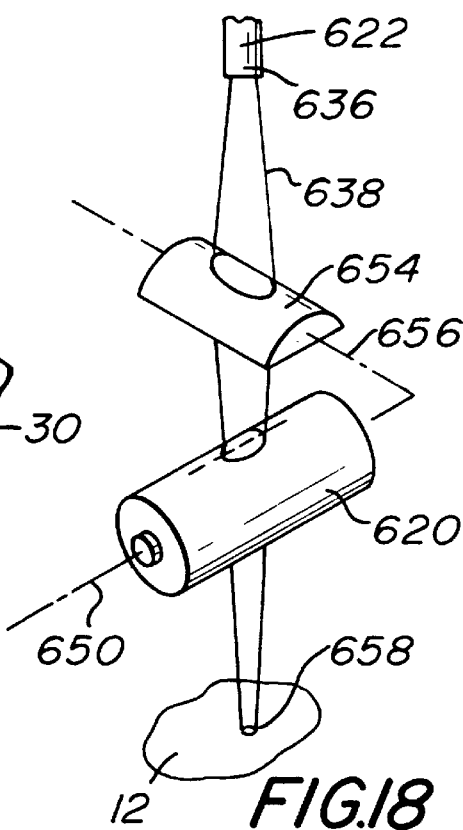
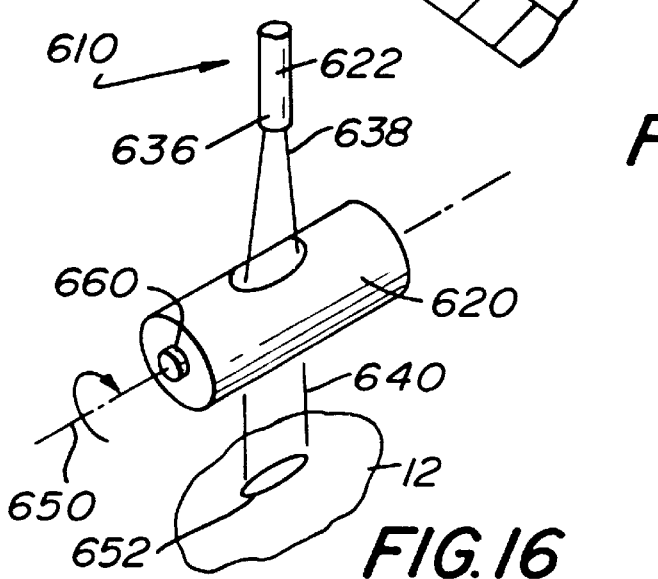
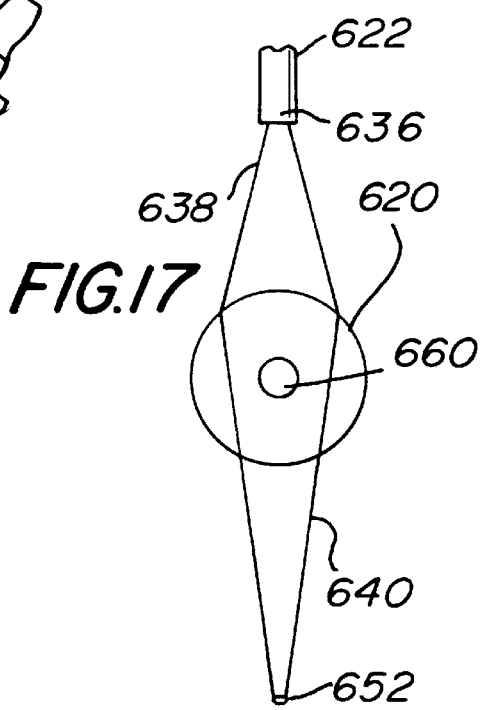

OPTICAL DELIVERY SYSTEM AND METHOD FOR SUBSURFACE TISSUE IRRADIATION

FIELD OF THE INVENTION

The present invention pertains to methods and apparatus for optically treating human or animal tissue by contact between an optical element and the tissue.

BACKGROUND OF THE INVENTION

Medical and surgical procedures using optical energy or light, such as laser energy, have been developed for a wide range of treatments. Historically, light was delivered to tissue to be treated in a direct line from the light source to the tissue by travelling through air. Subsequently, articulated arms, hollow wave guides, and fiber optics have provided more flexible and clinically suitable ways of delivering optical energy to tissue, but the energy still travelled through air before reaching the tissue. Delivery systems of this type are frequently referred to as non-contact delivery systems, since the delivery system is not intended to contact tissue in order to deliver energy to it. Although useful in many applications, non-contact delivery systems suffer from several drawbacks.

To overcome the drawbacks of non-contact delivery systems, numerous devices and techniques have been developed that permit direct contact between the delivery system and tissue, although both contact and non-contact delivery systems are used.

In recent years, attention has been given to the treatment of cutaneous tissue by optical energy. For example, U.S. Pat. No. 5,282,797 to Chess teaches a non-contact device and method for treating cutaneous vascular lesions by passing a laser beam through a cooling medium on its way to a patient's epidermis. The cooling medium is used to cool the patient's epidermis while it is being exposed to the laser beam. The need for a secondary device, such as a container to hold a cooling medium, separate from the laser delivery system makes the Chess apparatus and technique cumbersome. The coolant container must be frequently changed, since it will reach or exceed body temperature in a short time and become ineffective. The placement of a separate container between the delivery system and the tissue prevents tactile feedback to the surgeon manipulating the delivery system, and prevents the tissue from being compressed. It also alters the laser beam diameter and thus its power density.

U.S. Pat. No. 5,057,104, also to Chess, eliminates the coolant container and subjects the patient's epidermis to a cooling fluid. However, this patent also illustrates a non-contact device, i.e., there is no contact between the delivery system and the tissue, and thus it suffers from the same drawbacks as the device previously described. Moreover, as with all non-contact devices, it is difficult to keep the distance to tissue a constant and therefore the beam diameter, and thus power density, can change substantially.

U.S. Pat. No. 5,595,568 to Anderson, et al., discloses a method and apparatus for removing multiple hair follicles from skin. The method involves eliminating the hairs and follicles with optical energy delivered by a transparent tissue contact device. The apparatus includes an optically transparent contact device having a surface shaped to simultaneously contact several hair follicles in a region of the skin, and for delivering optical energy to a region of the skin, including the hairs and hair follicles. While the contact surface of the contact device is convex, sliding friction between the contact device and the surface of the skin can be problematic. The contact device is cooled by passing a cooling fluid over the rear surface of the contact device, i.e., the surface which does not contact the patient's skin. This is said to indirectly cool the patient's skin, but no direct cooling of the skin by a cooling fluid takes place.

U.S. Pat. No. 5,611,795 to Slatkine discloses a method of facial rejuvenation by using a carbon dioxide laser in conjunction with a flash scanner to ablate, or remove, an area of facial skin above the papillary dermis. There is no disclosure of any contact between the apparatus and the facial skin, which is consistent with the use of a carbon dioxide laser.

The present invention is intended to eliminate the drawbacks of the prior apparatus and methods. It is an object of the present invention to provide an effective apparatus and method to deliver sub-surface irradiation of tissue while providing the surgeon a greater degree of control over clinical effect. Another object of the invention is to provide tissue compression to give the surgeon the greater degree of control over the clinical effect obtained.

It is another object of the invention to provide subsurface irradiation of tissue with minimal surface temperature effects.

Another object of the invention is to provide an apparatus and method that provides direct cooling of the surface tissue while providing subsurface irradiation.

Yet another object of the invention is to provide low friction movement of the treatment apparatus over the tissue surface.

SUMMARY OF THE INVENTION

The present invention is directed to an apparatus for optically treating tissue by contact between the apparatus and the tissue. The apparatus comprises a holder having a distal end having an opening in it, and a contact member for contacting tissue to be treated and for coupling optical energy from a source of optical energy into said tissue. The contact member comprises a curved lens mounted in and partially extending from the opening and freely rotatable about at least one axis relative to the holder. The holder has a single coolant flow channel proximal to the opening of the contact member for supplying a cooling fluid to the contact member. A gap is provided between the contact member and the opening for allowing the fluid to flow around substantially the entire outer surface of the contact member and out of the opening onto said tissue to cool the tissue.

In one embodiment of the invention, a resilient member is provided proximal to said opening and resiliently biases said contact member toward said tissue. Preferably, but not necessarily, the resilient member is a constant force spring, so the that contact member is pressed against said tissue with a constant force.

The present invention also encompasses a method of optically treating tissue to effect heating of subsurface tissue while sparing excessive heating and resulting damage to the surface of the tissue, comprising the steps of contacting the surface of tissue in an area to be treated with a light transmissive low-friction contact optical element, applying optical energy from a source thereof to said optical element, converging said optical energy by said optical element into subsurface tissue in said area, moving said optical element over said area while maintaining it in contact with said surface, flowing a cooling fluid over said optical element and said surface to cool said optical element and said surface, and terminating application of optical energy to said optical element after a selected treatment time. In one embodiment of the invention, the optically treated subsurface tissue is delivered to induce dense new collagen growth.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 4 is a sectional view taken along the lines 4—4 in FIG. 2.

FIG. 5 is a side view on an enlarged scale, partially in section, of an apparatus according to a second embodiment of the invention.

FIG. 6 is a side view on an enlarged scale, partially in section, of the distal end of the apparatus shown in FIG. 5.

FIG. 7 is a side view on an enlarged scale, partially in section, of an apparatus according to a third embodiment of the invention.

FIG. 8 is a side view, partially broken away, showing a handpiece according to the second embodiment of the invention.

FIG. 9 is a side view, partially broken away and on an enlarged scale, of the handpiece illustrated in FIG. 8, showing relative movement of parts of the handpiece.

FIG. 10 is a sectional view, taken along the lines 10—10 in FIG. 8.

FIGS. 11–13 are side views on an enlarged scale, partially in section, of alternative designs according to the second embodiment of the invention.

FIG. 14 is a partial sectional view of a handpiece according to FIG. 8, showing one form of arrangement for measuring relative movement of parts of the handpiece.

FIG. 15 is a partial sectional view of a handpiece according to FIG. 8, showing an alternative form of arrangement for measuring relative movement of parts of the handpiece.

FIGS. 16 through 18 are schematic representations of an embodiment of the present invention using an alternative form of contact member.

DESCRIPTION OF THE INVENTION

Figure 1:
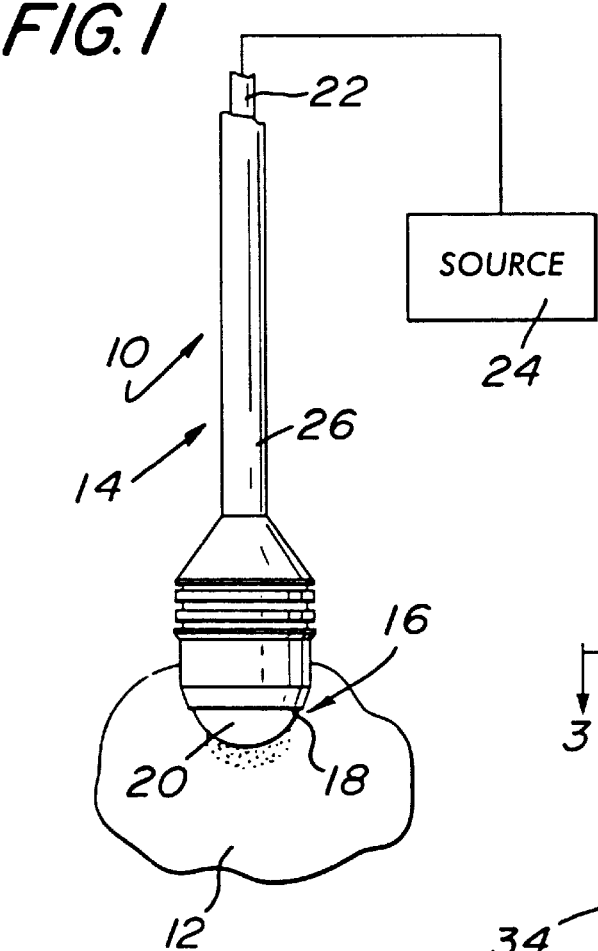
FIG. 1 illustrates a preferred form of apparatus according to the invention, shown in contact with tissue being treated.

Referring now to the figures, wherein like elements are indicated by like numerals, there is shown in FIG. 1 an apparatus 10 for optically treating tissue by contact with the tissue. Apparatus 10 is shown in contact with tissue 12, which for ease of understanding the illustrated embodiment is a patient's skin, although the present invention may be used to treat tissue other than skin. Generally, apparatus 10 comprises a holder 14 having a distal end 16. The distal end 16 has an opening 18, in which is mounted a tissue contact member 20. Tissue contact member 20 is spherical and is mounted for free rotation within distal end 16 of holder 14. In the embodiment illustrated in FIGS. 1 and 2, tissue contact member 20 is in the form of a spherical lens, which partially extends from opening 18, and which is freely rotatable about all axes relative to the holder 16. A fiber optic 22 is contained in holder 14, and serves to provide optical energy, such as laser energy, from a source 24 to contact member 20. Contact member 20 is optically transparent to the optical energy from the source, and is preferably made of fused silica, sapphire, or a suitable polymeric material. Source 20 may, but need not, be a laser, such as a CW, gated, or pulsed laser.

Figure 2:
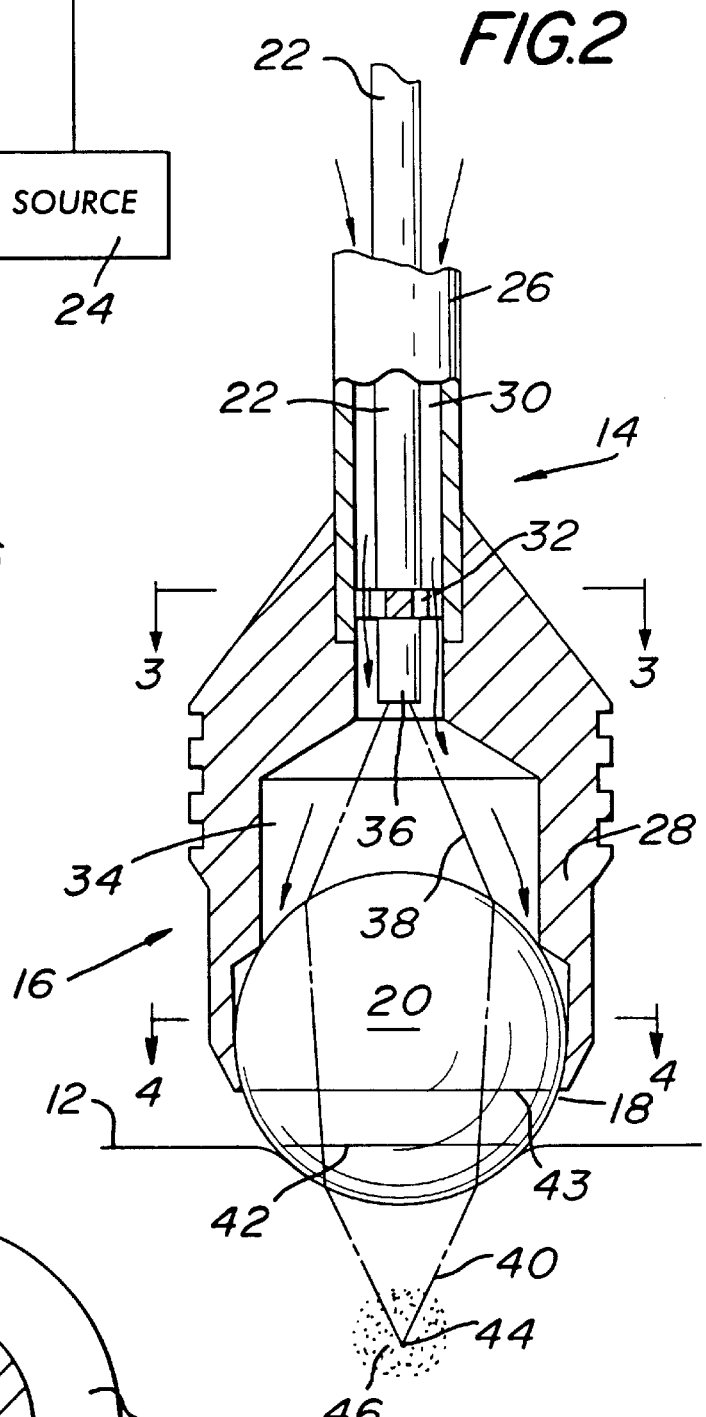
FIG. 2 is a side view on an enlarged scale, partially in section, of the apparatus of FIG. 1.
Figure 3:
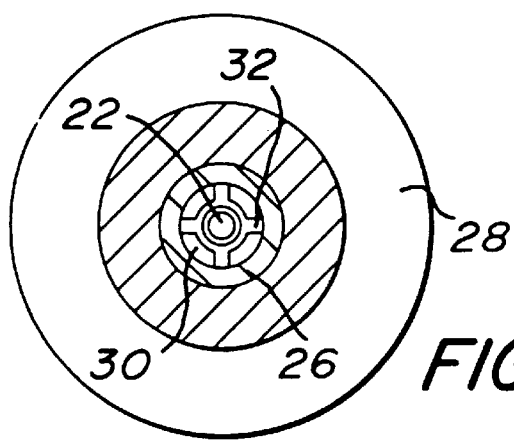
FIG. 3 is a transverse sectional view taken along the lines 3—3 in FIG. 2.

As best seen in FIG. 2, holder 14 preferably comprises an elongated portion 26 which is secured in a head portion 28 in which contact member 20 is mounted. Elongated portion 26 is hollow and surrounds fiber optic 22. Elongated portion 26 may, although need not, be in the form of a cylindrical tube, as illustrated. The inner diameter, or other inside dimension, of elongated portion 26 is larger than the outer diameter of fiber optic 22, so that there is a space, or channel, 30 between the inner wall of the elongated portion and the fiber optic 22. To aid in securing fiber optic within the channel 30, it may be held in place by a spider 32. Spider 32 supports the distal end of fiber optic 22, and maintains fiber optic 22 in coaxial relationship with holder 14.

Channel 30 defines a coolant flow channel, which permits a cooling fluid such as air, saline, a dextrose solution, or other suitable fluid, to be supplied to the distal end 16 of holder 14. As shown by the arrows in FIG. 2, cooling fluid flows through channel 30 and into a bore 34 in head portion 28. The cooling fluid substantially fills the bore 34. From there, the cooling fluid flows around substantially the entire outer surface of contact member 20 and out the opening 18 and onto the surface of the tissue 12 being treated. Although opening 18 will provide sufficient clearance between contact member 20 and distal end 16 for the coolant to flow out the opening 18, fluid flow may be facilitated by providing a plurality of circumferentially disposed grooves 48 in head portion 28 of distal end 16, as illustrated in FIG. 4. Grooves 48 can be dimensioned to provide a desired flow rate for various mediums, but they are not required, and thus they are not illustrated in all the figures.

The cooling fluid is not recirculated, but flows out freely out of distal end 16 onto the tissue 12. The cooling fluid serves several purposes. It primarily cools contact member 20 and head portion 28, so that heat generated during use (such as heating due to Fresnel losses or conducted heat) is removed. It both limits debris accumulation and washes debris and other foreign matter from the surface of fiber optic 22, keeping it free from deposits of tissue that may otherwise accumulate as a result of use. The cooled contact member 20 and the cooling fluid cool the surface of the tissue 12 in the area of contact member 20, so that thermal effects and thermal damage to the surface of the tissue are minimized. It acts as a lubricant for contact member 20 which, as noted above, is freely rotatable within distal end 16. And, when the cooling fluid is a liquid, the fluid which substantially fills bore 34 can serve to match the indices of refraction between the output end of fiber optic 22 and contact member 20, thus reducing Fresnel losses and consequent undesirable heat generation during use.

In operation, contact member 20 is placed in contact with the surface of tissue 12 to be treated. Where the tissue 12 is skin, for example, contact member 20 is placed in contact with the epidermis. Gentle force results in good optical contact with the tissue, and assures that the optically transparent region of the tissue contact member 20 is in touch with the tissue. Cooling fluid is supplied to holder 14 from a source (not shown) and the source 24 of optical energy is energized to supply optical energy to fiber optic 22. Source 24 is energized for a selected treatment time, i.e., for as long as necessary or desired for the particular procedure being performed. It should be understood that treatment time when using a gated or pulsed source is typically more than a single "on" cycle of source 24. For example, if source 24 is a gated laser, it will typically be cycled on and then off repeatedly during a given interval. Thus, treatment time encompasses a plurality of on/off cycles of a gated laser.

Fiber optic 22 conveys energy from source 24 in known manner to its output end 36, which is located in head portion 28 adjacent bore 34. The energy, typically but not necessarily laser light, is emitted from output end 36 as illustrated by the dashed lines 38 in FIG. 2. The energy is typically, although not necessarily, emitted from output end 36 in a divergent manner. The light is received by contact member 20, which gathers the light 38 emitted from the output end 36 of fiber optic 22 and tends to converge it into the tissue, as shown by the dashed lines 40. Depending upon the optical characteristics of the tissue 12, the light will converge as shown or will be altered by scattering within the tissue. Where scattering occurs, such as with skin tissue irradiated with near-infrared light, the refractive-caused convergence by contact member 20 will alter the volume of tissue irradiated by beam 40. No clinically significant optical energy is emitted from opening 18.

Preferably, the convergent beam 40 exiting the contact member 20 has a diameter less than or equal to the chord 42 of the contact member 20 across the area which contacts tissue 12, but absolutely less than the chord 43. This provides a precise optical coupling of the beam 40 with a larger area for tissue compression and tactile feedback to the surgeon. Contact member 20 can then be moved along and over the surface of tissue 12 as desired by the surgeon. Since contact member 20 is freely rotatable, it rolls over the surface of tissue 12, which may or may not be smooth, with minimal friction. The large chord 42 also permits a larger surface area for compression of the tissue 12. This results in better control of the light beam within tissue by expressing blood from vessels beneath contact member 20 that may absorb some or all of the light. The cooling fluid which flows around contact member 20 and out onto the surface of the tissue through opening 18 aids in reducing friction between contact member 20 and head portion 28 which secures contact member 20, and between contact member 20 and the surface of tissue 12.

The contact member 20 continuously acts to converge the beam emitted by output end 36 of fiber 22 as contact member 20 is rolled over the surface of tissue 12. The beam 40 reaches a focal region 44 below the surface of tissue 12. It should be noted, however, that beam 40 need not in all cases be convergent. If desired, other beam shapes can be attained by placing one or more additional optical elements, such as lenses or shaped fibers, between the output end 36 of fiber optic 22 and contact member 20. Thus, divergent beams, or beams with specific cross sections (such as circular, elliptical, and so forth), can be realized.

To ensure that sufficient energy reaches the focal region, the optical energy is preferably at wavelengths which will penetrate the tissue to a desired depth. For example, if tissue 12 is skin, the wavelength would be chosen to penetrate to subdermal structures with minimal absorption by the epidermis. The wavelength is also chosen to provide more or less scatter, as may be desired by the surgeon. Scatter may be thought of as numerous small reflections within tissue which result in the random deflection of light from its original angle of incidence. Thus, the beam 40 will expend its energy in a somewhat larger and more diffusely shaped volume of tissue when compared to a less scattering tissue medium or a non-contact (air) path. Since scatter is principally a wavelength-dependent phenomenon, the wavelength of the optical energy may be chosen for a desired amount of scatter.

By focusing the beam 40 below the surface of the tissue, the intensity of the beam per unit volume of tissue at the tissue surface region will be minimized and the subsurface intensity per unit volume will be increased. Therefore, the distribution of energy absorbed by subsurface structures can be controlled. It is the energy absorbed and converted to heat by the subsurface structures, which provides the desired therapeutic effect. By controlling the depth to which beam 40 penetrates tissue 12, subsurface therapeutic effects can be achieved while minimizing surface temperature effects 46.

It has long been known that therapeutically useful changes in the spot size of a non-contact beam of light in a scattering tissue may result in the absence of change in the desired effect. In other words, the surgeon cannot cause small changes in the delivered beam of light and cause a therapeutically useful change in the treated volume within tissue. However, by using the present invention it has been found that the distribution of energy and its absorption by tissue can be affected by the amount of force with which contact member 20 is pressed against the tissue. Even though scatter is essentially constant for a given wavelength, the effect of scatter can be affected by compressing the tissue. This occurs when the contact element 20 applies sufficient force on the tissue and reduces the path length of the energy in the tissue. When contact member 20 is placed in contact with the tissue, the volume of tissue being treated decreases as the contact member 20 is pressed harder onto the tissue. There is a region where the reduction in the scattered volume effect is proportional to the distance contact member 20 is pressed into the tissue. Therefore, the surgeon can affect the volume of treated tissue, and the resulting therapeutic effect provided by the present invention, by simply pressing the contact member 20 with more or less force onto the tissue being treated.

An alternative form of apparatus according to a second embodiment of the invention is illustrated in FIGS. 5 and 6. In the second embodiment illustrated in those figures, distal end 116 of holder 114 is essentially the same as distal end 16 of holder 14 according to the first embodiment. Distal end 116 may, but need not, include an annular shoulder 118 within bore 34, which acts as a seat for a resilient member such as a coil spring 120. Shoulder 118 may be dispensed with, if desired, and coil spring 120 may seat directly against the proximal surface 119 of bore 34. Coil spring 120 engages either shoulder 118 or proximal surface 119 at one end and contact member 20 at the other end, and biases contact member 20 against opening 18, as best seen in FIG. 6. Coil spring 120 is preferably a constant force spring, so that it applies a constant force on contact member 20 regardless of the extent to which it is compressed.

In the position illustrated in FIG. 6, contact member 20 is not in contact with tissue, but may be considered suspended in air. In that position, contact member 20 is biased against the perimeter of opening 18, and thus can act to effectively seal opening 18 so that no fluid flows out of it. Thus, contact member 20 can, if desired, act as a valve to regulate the flow of cooling fluid from distal end 116.

When distal end 116 is placed in contact with tissue 12, as illustrated in FIG. 5, tissue 12 exerts a counterforce on contact member 20, against the biasing force exerted on contact member 20 by spring 120. This partially compresses spring 120, and allows contact member to move away from opening 18. This, in turn, allows contact member to rotate freely with cooling fluid flowing out from opening 18. An advantage of resiliently biasing contact member 20 toward opening 18 is that it compensates for uneven surfaces on tissue 12, and compensates for different surgeons, who may press contact member 20 against the surface of tissue 12 with more or less force. If the surgeon applies more force, spring 120, which is preferably a constant force spring, applies a constant force on contact member 20. Consequently, contact member 20 maintains a constant pressure against the tissue, independent of the force applied by the surgeon. In this manner, contact member 20 is maintained in optimum contact with the tissue and allows for variations in surgical techniques and applied forces.

Different force biasing can be chosen to achieve different degrees of tissue compression for different size contact members. The surgical application and the size of contact member 20 will dictate the pressure that will be useful. In cosmetic treatments on skin around the eye, for example, pressures in the range from about 1.5 psi to about 5 psi were found useful. In similar treatments around the abdomen, pressures in the range from about 10 psi to about 20 psi were effective. It must be noted that factors such as power, wavelength, absorption, and duration of the light used will affect the optimal pressure.

A third embodiment of the invention is illustrated in FIG. 7. In the embodiment illustrated in FIG. 7, distal end 216 of holder 214 is essentially the same as distal end 16 of holder 14. However, in the embodiment of FIG. 7, optical energy is not conveyed from a remote source by a fiber optic, as in the previous embodiments, but is generated within distal end 216 by a light emitting electronic device such as a laser diode 218 mounted on spider 32. Laser diode 218 may be energized by means of wire leads 220, which are connected to a controllable source of electrical power (not shown). Laser diodes are known per se in the art, and need not be described in detail. It is sufficient to note that the particular laser diode used may be chosen to provide whatever wavelength and power output may be desired for a particular surgical procedure. The unique asymmetric beam profiles inherent in laser diodes can be optimized for a particular application.

Another embodiment of the invention is illustrated in FIGS. 8 through 10. In that embodiment, the invention 300 comprises a handpiece 302 and a wand 304. Handpiece 302 and wand 304 are relatively movable along the longitudinal axis of handpiece 302, so that wand 304 may extend from or be retracted into the distal end 306 of handpiece 302. Wand 304 comprises an elongated portion 26 which carries distal end 16 from which extends tissue contact member 20. For purposes of understanding the embodiment illustrated in FIGS. 8 through 10, distal end 16 and its parts may be considered to be the same as shown in FIG. 2.

Elongated portion 26 is located within wand 304 and includes a fluid coolant flow channel 30. Elongated portion 26 supports fiber optic 22, such as by spider 32, as in the embodiment illustrated in FIG. 2.

Handpiece 302 is provided with an internal increased diameter bore 308 which is coaxial with channel 30 and in which is located a resilient biasing member 310. In the illustrated embodiment, biasing member 310 is shown in the form of a coil spring. Preferably, biasing member 310 is a constant force spring, so that a constant force is exerted on contact member 20 regardless of the extent to which biasing member 310 is compressed. The biasing member provides uniform force on the tissue and compensates for uneven surfaces on tissue 12, and compensates for different surgeons, who may press contact member 20 against the surface of tissue 12 with more or less force. Constant force springs and biasing mechanisms are known per se, and therefore do not need to be described here in further detail.

As best seen in FIG. 9, one end of the resilient biasing member 310 seats against the proximal end wall 312 of bore 308. The opposite end of biasing member seats against an annular collar 314 on a portion of wand 304 which extends into distal end 306 of handpiece 302. Collar 314 also serves as a stop to limit the distance which wand 304 may extend from handpiece 302. As the surgeon grasps handpiece 302 and presses contact member 20 against the tissue 12, the surgeon will apply more or less force on wand 304, thus compressing resilient biasing member 310 to a greater or lesser extent. This will cause wand 304 to move inwardly and outwardly with respect to handpiece 302, as indicated by the double-headed arrow in FIG. 9. Moreover, since biasing element 310 is a constant force spring, it absorbs differences in force that different surgeons may apply, so that the contact member 20 applies a constant force to the tissue 12. Thus, wand 304 "floats" with respect to handpiece 302.

Some variations on the resiliently biased wand embodiment are illustrated in FIGS. 11 through 13. In those figures, the wand 304 does not float relative to the handpiece, but rather the head portion floats relative to the wand 304. Thus, in FIG. 11, there is illustrated an elongated head portion 316 which moves in and out of wand 304, as indicated by the double-headed arrow in FIG. 11. Head portion 316 has an increased diameter portion 318, which has an outer diameter just slightly less than the inner diameter of wand 304, and a decreased diameter neck portion 320 which slides in and out of an opening 322 in the distal end 324 of wand 304. Head portion has an angled shoulder portion 326 which cooperates with an angled inner face 328 on wand 304 to limit the outward extension of head portion 316.

The increased diameter portion 318 of head portion 316 has in inner bore 332 in which resilient biasing element 310 is seated. Biasing element 310 is seated between the distal end of bore 332 and the end wall 336 of wand 304. Biasing element 310 is shown partially compressed in FIG. 11 (and in FIGS. 12 and 13). When no force is applied to head portion 316, biasing element urges head portion 316 outwardly from wand 304 until shoulder 326 abuts inner face 318. When pressure is applied to head portion 316, biasing element 310 is compressed, and allows head portion to move inwardly, until the proximal end 334 contacts end wall 336 on wand 304.

FIG. 12 shows a variation which is in its essential respects the same as the variation shown in FIG. 11, except that head portion 416 has a much shorter axial length than head portion 316. The variation shown in FIG. 13 is essentially the same as that shown in FIGS. 11 and 12, except that wand 504 has an angled bend 506.

In some cases, either because a particular procedure demands it or because a particular surgeon prefers to have a more quantitative idea of the force he is applying to the handpiece, it is desirable to provide some indication to the surgeon of the applied force in addition to the tactile feedback inherent in a contact device. FIG. 14 illustrates one manner of indicating the applied force to the surgeon. As illustrated in FIG. 14, the elongated portion 26, or the outer surface of wand 304, may be marked with a position-indicating code 520, which may be a bar code, for example, or another code suitable for indicating the extent of relative movement of wand 304 relative to handpiece 302 and, thus, the applied force. Movement of wand 304 may be sensed photo-optically by a photo-optic sensor 522 located adjacent the code 520. Power and signal connections to sensor 522 may be made through wires 524. The signal output of sensor 522 may be used to provide an audible, visual, or other output which may be sensed by the surgeon. For example, the signal output may be used to generate a tone whose frequency is dependent on the relative positions of wand 304 and handpiece 302. The signal output may also be used to illuminate a series of LEDs 528, which may be mounted on handpiece 302. The number of LEDs illuminated, or their relative brightnesses, can be used to indicate relative position of the wand 304 and the handpiece 302.

A direct visual approach to sensing the relative positions of the wand 304 and handpiece 302 is illustrated in FIG. 15. In FIG. 15, the jacket of fiber optic 22, or the outer surface of wand 304, is marked with a position-indicating code 520, which may be a series of bars as illustrated, or which may be any other suitable code for indicating the extent to which wand 304 has moved relative to handpiece 302. In the embodiment illustrated in FIG. 15, a view port or window 530 is provided to give the surgeon direct visual access to the code 520. Thus, the surgeon can see at a glance how the wand 304 is positioned relative to the handpiece 302. As another alternative, either one of wand 304 or handpiece 302 may be marked with a reference mark, and the other may be marked with a plurality of spaced hash marks to indicated relative movement, in the manner of a slide scale.

The present invention has been illustrated in the foregoing embodiments using a spherical contact member 20. Although a spherical contact member is generally preferred, the invention is not limited to a spherical element. There are situations where other contact members having a curved surface may be desirable, and even preferable over a sphere. One such alternative contact member is illustrated in FIGS. 16 through 19. The alternative embodiment 610 depicted in those figures uses a contact member 620 which is in the form of a right circular cylinder. In the schematic representation illustrated in FIGS. 16 through 18, the contact member is journaled for rotation about its longitudinal axis 650, as indicated by the arrow in FIG. 16.

Fiber optic 622 conveys energy from a source to its output end 636, which is located adjacent contact member 620. The energy, typically but not necessarily laser light, is emitted from output end 636 as illustrated by the lines 638 in FIG. 16. The energy is typically, although not necessarily, emitted from output end 636 in a divergent manner. The light is received by contact member 620, which gathers the light 638 emitted from the output end 636 of fiber optic 622 and transmits it to the tissue, as shown by the dashed lines 640. The shape of the cylinder projects the light 640 onto tissue 12 in the shape of an elongated oval spot 652. This type of spot may be preferred in certain procedures where broad coverage is desired. Alternatively, the light source can be a diode laser (not shown) instead of fiber optic 622. The asymmetric beam profile inherently emitted from a laser diode source may be advantageously coupled to contact member 620.

The shape of the spot projected onto the tissue 12 can be altered, if desired, by using additional optics such as lens 654 between the output end 636 of fiber optic 622 and contact member 620. One such arrangement is illustrated in FIG. 18. For example, a partially cylindrical lens 654, arranged with its longitudinal axis 656 perpendicular to the longitudinal axis 650 of contact member 620, produces a spot 658 which is generally circular. Other arrangements which project different spot shapes, are possible and within the scope of the skilled artisan.

Figure 19:
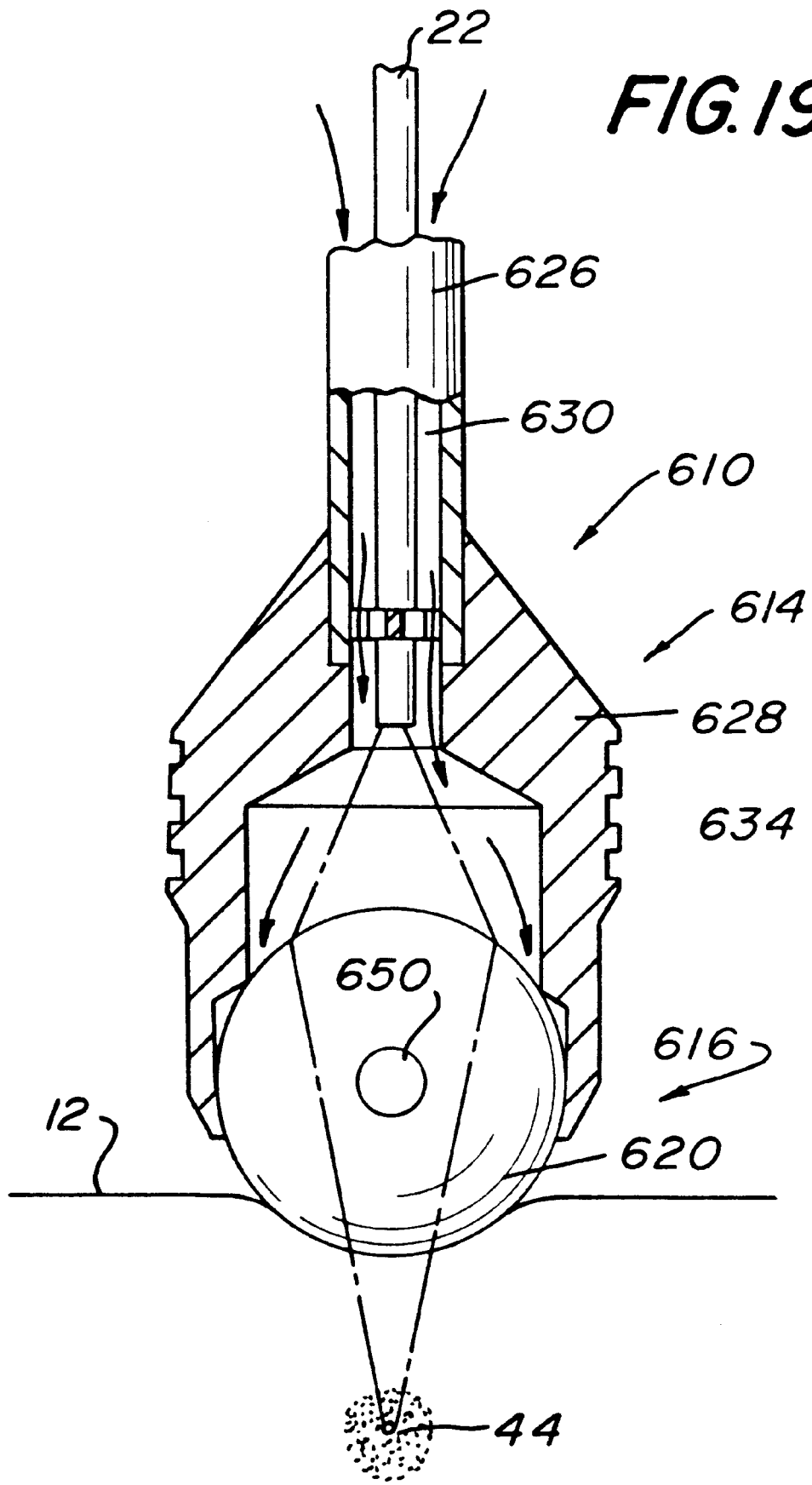
FIG. 19 is a side view on an enlarged scale, partially in section, of an apparatus employing the alternative form of contact member illustrated in FIGS. 16–18.

FIG. 19 illustrates one way in which a device 610 using a cylindrical tissue contact member 620 may be constructed. As with the embodiment illustrated in FIG. 2, device 610 comprises a holder 614 and an elongated portion 626 which is secured in a head portion 628 in which contact member 620 is mounted. As mentioned previously, contact member 620 is journaled for rotation about its longitudinal axis 650, and any suitable manner of supporting contact member 620 for such rotation is within the scope of the invention. For example, contact member 620 may be provided with axial bosses 660 on its end faces (see FIG. 16), which are received in corresponding bores or indentations in the interior wall of head portion 628. Alternatively, bosses may be provided on the interior wall of head portion 628 and corresponding indentations provided in the end faces of contact member 620, so that contact member 620 snaps into place within head portion 628. Any manner of supporting contact member 620 for rotation about its longitudinal axis may be used without departing from the scope of the present invention.

Elongated portion 626 is hollow and surrounds fiber optic 22. The inner diameter, or other inside dimension, of elongated portion 626 is larger than the outer diameter of fiber optic 22, so that there is a space, or channel, 630 between the inner wall of the elongated portion and the fiber optic 22. To aid in securing fiber optic within the channel 630, it may be held in place by a spider 632 which supports the distal end of fiber optic 22, and maintains fiber optic 22 in coaxial relationship with holder 614.

Channel 630 defines a coolant flow channel, which permits a cooling fluid to be supplied to the distal end 616 of holder 614. As in the previously described embodiments, cooling fluid flows through channel 630 and into a bore 634 in head portion 628. The cooling fluid substantially fills the bore 634. From there, the cooling fluid flows around substantially the entire outer surface of contact member 620 and out of distal end 616 onto the surface of the tissue 12 being treated. Outward fluid flow may be facilitated by providing a plurality of circumferentially disposed grooves in head portion 628 of distal end 616, as described previously in connection with FIG. 4.

Although the present invention is not limited to any specific surgical procedure, the invention has great utility in delivering a photocoagulation effect in the upper dermis while sparing the epidermis. The system is intended to provide increased skin tone and subsurface (dermis) collagen formation without the surface damage seen with other laser systems which treat only the surface.

Figure 20A:
FIGS. 20A, 20B, and 20C are photographs of histopathologic sections of tissue showing changes over time induced by delivery of energy in accordance with the apparatus and method of the invention.

In vitro studies of the invention have demonstrated clinically relevant acute skin contraction and chronic new collagen formation. The treatment result, as seen in FIG. 20A on histopathology, in an acute zone of thermal damage limited to a small area of the superficial dermis. Visible is a thin zone of coagulated collagen beneath the healthy epithelium. This is in contrast to other approaches to skin remodeling with lasers, which show full thickness epidermal damage. Such damage has previously been necessary in order to reach the dermis.

Preliminary investigations of the invention included in vitro studies on human breast skin and eyelids. The studies considered and compared the acute skin shrinkage measurements resulting from the treatment with the invention with findings from $CO_2$ laser treatment. The shrinkage from the $CO_2$ laser study was compared with published values for skin shrinkage from carbon dioxide laser resurfacing. The agreement between these measurements and publish values was very good.

The shrinkage of the breast skin with the invention was measured for a given nominal intensity, 85% and 75% of the nominal intensity. In all cases, the shrinkage increased linear early with the number of laser passes. The shrinkage observed using the $CO_2$ laser was approximately the same as the nominal or 85% of nominal intensity using the present invention Histological analysis of the in vitro skin treated with the invention showed about 300 $\mu$m of photocoagulated collagen below a relatively intact epidermal layer. This compares with roughly 100 $\mu$m of thermally damaged collagen and the complete loss of the epithelium with the carbon dioxide resurfacing.

Figure 20B:
Figure 20C:

FIG. 20B shows a histologic sample of tissue with a thermal injury induced according to the method of the present invention. The sample was taken six days postoperatively. The healthy epidermis remains. The denatured collagen is digested with some collagen present. FIG. 20C shows a sample taken at 21 days. Again, the healthy epidermis remains. The denatured collagen is digested and dense new collagen is present.

Tissue changes caused by the carbon dioxide laser: Experiments to measure the contraction of skin followed the methods given in In Vitro studies (see Gardner, E., Reinisch, L., Stricklin G. P., and Ellis, D. L., "In vitro changes in Non-Facial Human Skin Following $CO_2$ laser resurfacing: A comparison study." *Lasers Surg. Med.* 19: 379–387 (1996))

The histology micrographs were examined to assess the damage to the skin following carbon dioxide treatment. The samples were stored in 10% formalin and prepared with a Mason's trichrome stain by usual techniques. The histology reveals that the epithelium had been removed. A zone of thermal damage is observed on the surface of the skin with charring on the edge. In typical fresh-frozen breast skin, the zone of thermal damage is measured to be 100±20 microns thick. The eyelid tissue following five laser passes showed no epithelium and 155±35 microns of thermal damage. The eyebrow tissue also showed no epithelium with 120±25 microns of thermal damage. The shrinkage measured in this study with breast tissue was compared to a previously published study using two other carbon dioxide lasers (Gardner, et al., *Lasers Surg. Med.* 19: 379–387 (1996)). The other study used the Sharplan Silktouch™ and the Coherent Ultrapulse™ lasers. No differences were seen between these two lasers. Within the errors of the measurements, the measurements of shrinkage were the same.

Tissue chances caused by the invention: All tissue was obtained from fresh-frozen breast reduction tissue. Following the methods of Gardner et al., 1996, the tissue was re-hydrated before each measurement with a cotton-tipped applicator soaked in sterile saline. The distance between the points placed on the tissue prior to treatment were measured. There was a linear fit to the data points.

Histologic photomicrographs were prepared with a Mason's trichrome stain using standard techniques. The fresh-frozen human breast skin samples were treated with two passes of the invention. The histology reveals that the epithelium is preserved, and the cells appear to be intact. A zone of the thermal damage is seen directly below the epithelium. This zone extends down into the dermis a distance of 200±100 microns when measured from the surface of the skin. Obviously, this zone can be extended or reduced by alterations in the delivered fluence. Acutely, below the epidermal layer is a zone of thermally denatured collagen. Over time, the epidermal layer is not lost by thermal damage. The denatured collagen and connective tissue is digested and replaced by dense new collagen in the dermis. This dense band of collagen beneath an undisrupted epidermis results in skin having a more youthful appearance.

Figure 21A:
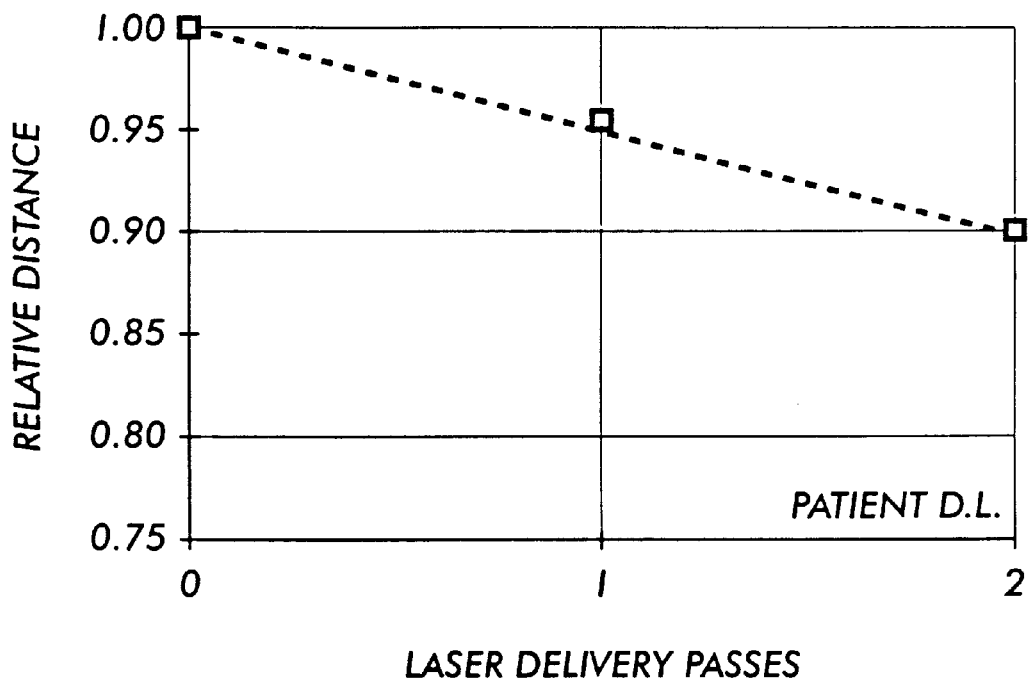
FIGS. 21A and 21B show actual acute shrinkage in two patients induced in skin.
Figure 21B:
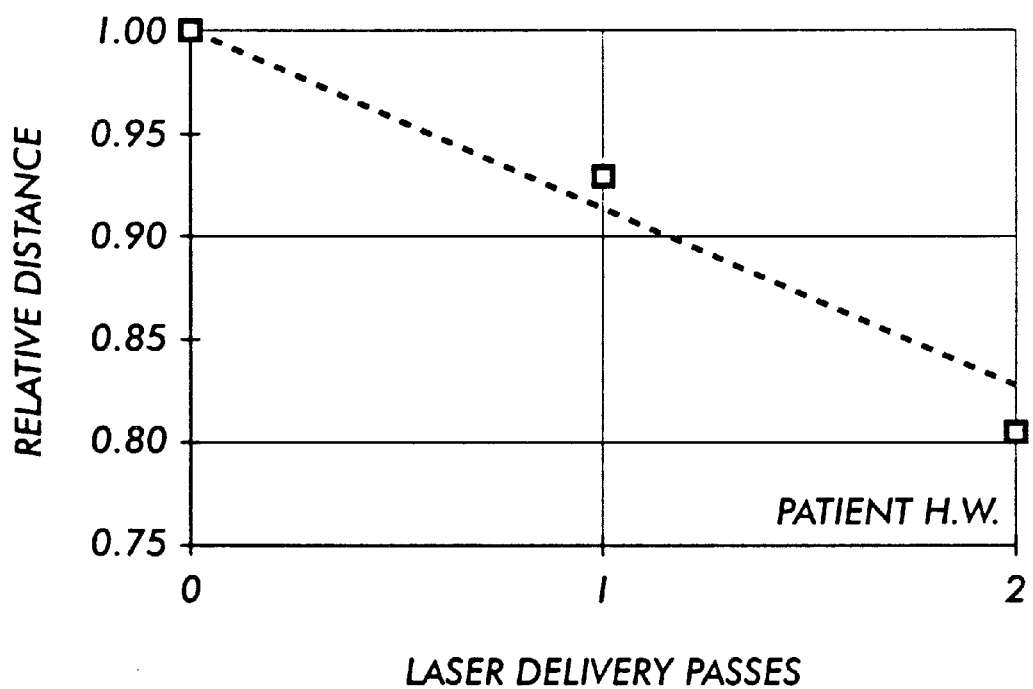

Freeze-frame computer software and hardware was used to determine the amount of skin shrinkage. The results show that the invention produces a decrease in measured relative skin length (clinically observed as skin contraction or tightening) which occurs linearly as a function of the number of passes or treatments applied. FIGS. 21A and 21B show acute facial tissue shrinkage for two patient trials. In both cases, two passes of energy were delivered. As shown, the result was shrinkage of approximately 5.5% per pass, without epidermal damage. In summary, greater applied intensity produces more contraction, and each additional pass produces contraction similar to that produced by the previous pass.

The present invention may be embodied in other specific forms without departing from the spirit or essential attributes thereof and, accordingly, reference should be made to the appended claims, rather than to the foregoing specification, as indicating the scope of the invention.

We claim:

1. An apparatus for optically treating tissue by contact between the apparatus and the tissue, comprising a holder having a distal end having an opening therein, a contact member for contacting tissue to be treated and for coupling optical energy from a source thereof into said tissue, said contact member comprising a curved lens mounted in and partially extending from said opening and freely rotatable about at least one axis relative to the holder, a single coolant flow channel proximal to said opening and said contact member for supplying a cooling fluid to said contact member, and a gap between said contact member and said opening for allowing said fluid to flow around substantially the entire outer surface of said contact member and out of said opening onto said tissue to cool said tissue.

2. An apparatus for optically treating tissue according to claim 1, wherein the contact member comprises a cylinder mounted for rotation about its longitudinal axis.

3. An apparatus for optically treating tissue according to claim 1, wherein the contact member comprises a sphere mounted for free rotation about all axes.

4. An apparatus for optically treating tissue according to claim 1, further comprising at least one fluid outlet groove in said holder adjacent said contact member.

5. An apparatus for optically treating tissue according to claim 1, wherein said fluid is a liquid.

6. An apparatus for optically treating tissue according to claim 1, wherein said fluid is a gas.

7. An apparatus for optically treating tissue according to claim 1, further comprising a fiber optic conduit for conveying said optical energy from said source to said contact member for coupling into said tissue.

8. An apparatus for optically treating tissue according to claim 1, further comprising a source wherein said source is a directly coupled diode laser.

9. An apparatus for optically treating tissue by contact between the apparatus and the tissue, comprising a holder having a distal end having an opening therein, a contact member for contacting tissue to be treated and for coupling optical energy from a source thereof into said tissue, said contact member comprising a curved lens mounted in and partially extending from said opening and freely rotatable about at least one axis relative to the holder, a resilient member proximal to said opening and resiliently biasing said contact member toward said tissue, a single coolant flow channel proximal to said opening and said contact member for supplying a cooling fluid to said contact member, and a gap between said contact member and said opening for allowing said fluid to flow around substantially the entire outer surface of said contact member and out of said opening onto said tissue to cool said tissue.

10. An apparatus for optically treating tissue according to claim 9, wherein the contact member comprises a cylinder mounted for rotation about its longitudinal axis.

11. An apparatus for optically treating tissue according to claim 9, wherein the contact member comprises a sphere mounted for free rotation about all axes.

12. An apparatus for optically treating tissue according to claim 9, wherein the resilient member comprises a spring.

13. An apparatus for optically treating tissue according to claim 12, wherein the spring comprises a coil spring.

14. An apparatus for optically treating tissue according to claim 12, wherein the spring comprises a constant force spring.

15. An apparatus for optically treating tissue according to claim 14, wherein the constant force spring enables said contact member to exert a substantially constant compressive force on said tissue.

16. An apparatus for optically treating tissue according to claim 9, further comprising a handpiece and said holder comprising a wand movable relative to said handpiece along a common axis, said resilient member acting on said wand to bias said wand and said contact member toward said tissue.

17. An apparatus for optically treating tissue according to claim 16, further comprising an indicator for indicating relative movement of said wand with respect to said handpiece.

18. An apparatus for optically treating tissue according to claim 17, wherein the indicator comprises indicia on one of said wand and said handpiece to provide a direct visual indication of said relative movement.

19. An apparatus for optically treating tissue according to claim 17, wherein the indicator comprises indicia on said wand and a photo-optic sensor on said handpiece for monitoring movement of said indicia relative to itself and generating a signal representative of said movement.

20. An apparatus for optically treating tissue according to claim 19, further comprising an audible tone generator responsive to said signal for generating a tone whose pitch is a function of said movement.

21. An apparatus for optically treating tissue according to claim 19, further comprising an optical display responsive to said signal for generating a visual signal which is a function of said movement.

22. A method of optically treating tissue to effect heating of subsurface tissue while sparing excessive heating to the surface of said tissue, comprising the steps of contacting the surface of tissue in an area to be treated with a light transmissive low-friction contact optical element mounted for rotation in a holder, applying optical energy from a source thereof to said optical element, converging said optical energy by said optical element into subsurface tissue in said area, causing said optical element to rotate within said holder while moving said optical element over said area and maintaining it in contact with the surface of said tissue, flowing a cooling fluid over said optical element and said surface to cool said optical element and said surface, and terminating application of optical energy to said optical element after a selected treatment time.

23. A method of inducing collagen synthesis beneath an undisrupted epidermis in human skin, comprising the steps of contacting the surface of tissue in an area to be treated with a light transmissive contact optical element, applying optical energy from a source thereof to said optical element mounted for rotation in a holder, converging said optical energy by said optical element into subsurface tissue in said area, causing said optical element to rotate within said holder while moving said optical element over said area and maintaining it in contact with the surface of said tissue, flowing a cooling fluid over said optical element and said surface to cool said optical element and said surface, and terminating application of optical energy to said optical element after a selected treatment time.

* * * * *